(12) United States Patent
MacCraith et al.

(10) Patent No.: US 7,750,316 B2
(45) Date of Patent: Jul. 6, 2010

(54) POLYMER BIOCHIP FOR DETECTING FLUORESCENCE

(75) Inventors: Brian MacCraith, Dublin (IE); Thomas Ruckstuhl, Zurich (CH)

(73) Assignee: Dublin City University, Dublin (IE)

( * ) Notice: Subject to any disclaimer, the term of this patent is extended or adjusted under 35 U.S.C. 154(b) by 383 days.

(21) Appl. No.: 11/431,349

(22) Filed: May 10, 2006

(65) Prior Publication Data

US 2007/0262265 A1 Nov. 15, 2007

(51) Int. Cl.
*G01N 21/64* (2006.01)
(52) U.S. Cl. .................................................. 250/461.2
(58) Field of Classification Search ............ 250/461.1, 250/461.2, 458.1, 208.2; 356/244
See application file for complete search history.

(56) References Cited

U.S. PATENT DOCUMENTS

| | | | | |
|---|---|---|---|---|
| 4,638,110 A | * | 1/1987 | Erbert | 136/246 |
| 4,649,280 A | * | 3/1987 | Holland et al. | 250/483.1 |
| 4,810,658 A | * | 3/1989 | Shanks et al. | 436/172 |
| 5,006,716 A | * | 4/1991 | Hall | 250/458.1 |
| 5,192,510 A | * | 3/1993 | Zoha et al. | 422/82.05 |
| 5,779,978 A | * | 7/1998 | Hartmann et al. | 422/82.05 |
| 5,841,143 A | * | 11/1998 | Tuma et al. | 250/458.1 |
| 6,521,882 B1 | * | 2/2003 | Sumiya et al. | 250/208.2 |
| 6,714,297 B1 | | 3/2004 | Ruckstuhl et al. | |
| 6,987,259 B2 | * | 1/2006 | Olszak et al. | 250/208.1 |
| 7,046,357 B2 | * | 5/2006 | Weinberger et al. | 356/246 |
| 7,158,224 B2 | * | 1/2007 | Montagu | 356/244 |
| 7,262,859 B2 | * | 8/2007 | Larson et al. | 356/445 |
| 2002/0197456 A1 | * | 12/2002 | Pope | 428/209 |
| 2003/0094564 A1 | * | 5/2003 | Verdonk et al. | 250/208.2 |
| 2004/0058407 A1 | * | 3/2004 | Miller et al. | 435/29 |
| 2004/0124336 A1 | * | 7/2004 | MacCraith et al. | 250/208.2 |
| 2004/0125370 A1 | * | 7/2004 | Montagu | 356/244 |
| 2006/0092532 A1 | * | 5/2006 | Ouderkirk et al. | 359/819 |

FOREIGN PATENT DOCUMENTS

| | | |
|---|---|---|
| WO | WO 02/059583 A1 | 8/2002 |
| WO | WO 03/023377 A1 | 3/2003 |

\* cited by examiner

*Primary Examiner*—David P Porta
*Assistant Examiner*—Faye Boosalis
(74) *Attorney, Agent, or Firm*—Mark S. Leonardo; Brown Rudnick LLP

(57) ABSTRACT

This present disclosure provides an optical chip for fluorescence detection. The optical chip has one or more parabolic optical elements that capture and collimate the fluorescent light and direct it onto a detector. The optical chip may be constructed of a polymer and made using injection molding techniques.

16 Claims, 6 Drawing Sheets

POLYMER BIOCHIP FOR DETECTING FLUORESCENCE

BACKGROUND

1. Technical Field

This present disclosure relates to an optical chip for detecting fluorescence and optical sensor configurations that utilize an optical chip.

2. Description of the Related Art

There is an increasing requirement to detect a wide range of biological analytes in an aqueous environment with high sensitivity. Lab-on-a-chip designs are widely used for simultaneous and parallel detection of multiple analytes. Most sensors use an optical chip having surface-bound molecules such as antibodies or oligonucleotides that can specifically bind the analytes of interest found in the aqueous solution that flows over the sensors. The sensors typically consist of a substrate having a luminescence emitter in optical contact with the optical detection device. The emitter may transmit luminescence directly into the detection device, or it may require activation by another means (e.g., incident "excitation" light or a chemical reaction).

The majority of current sensor designs have limited sensitivity because they employ rather inefficient techniques for the collection of luminescence emitted by thin sensing films and surface-attached molecules. The problem of low luminescence intensity has been addressed in a variety of ways. For example, the incorporation of metal coatings or metal nanoparticles into sensors increase the intensity of luminescence emitted by molecules in the vicinity of the metal. This technique has been shown to enhance the quantum yield by 100-1000 fold. While somewhat successful, these methods address only increasing the magnitude of the fluorescent signal. Little progress has been made to increase the efficiency of the luminescence collection.

The most sensitive detection technique in widespread use is fluorescence microscopy which is capable of single molecule detection (SMD). Widespread application of SMD is limited because of the expense of the microscope required and its lack of portability. Thus, there is a need for inexpensive, portable, and sensitive devices for fluorescence detection.

SUMMARY

The present invention provides an optical chip comprising a plurality of optical elements, wherein the optical elements (a) have parabolic shape such that light entering an optical element at the detection surface at an angle greater than a $\theta_{min}$ is totally internally reflected and substantially collimated along the axis perpendicular to said detection surface, (b) have a detection moiety optically linked to the detecting surface, (c) each have a corresponding annular aperture, and wherein the optical chip comprises a polymer having a refractive index ($n_p$) greater than the refractive index of water. The annular aperture is configured such that light entering an optical element at an angle less than the $\theta_{min}$ impinges on the aperture and does not reach the detector. Optionally, the annular aperture may be configured such that light entering an optical element at an angle greater than a $\theta_{max}$ also impinges on the aperture and is prevented from reaching the detector. Useful values for $\theta_{min}$ include angles of about 55° to about 70°, but typically are about 62°. Useful values for $\theta_{max}$ include angles of about 75° to about 85°, but typically are about 80°.

The optical chip of the invention is formed of a polymer having a refractive index greater than that of water. Useful polymers have a refractive index of about 1.45-1.65. Useful polymers include ZEONEX which has a refractive index of about 1.52.

The detection surface of the optical elements may have a detection moiety that is optically coupled to the optical element. Suitable detection moieties are any molecules that specifically bind to an analyte of interest and include, for example, antibodies and oligonucleotides. The optical elements of a chip may comprise the same or different detection moieties depending upon the application.

The invention also provides a luminescent sensor configuration comprising (a) an excitation light source, (b) a chip comprising a plurality of parabolic optical elements, wherein each optical element has a detection moiety optically linked to the detecting surface, and is capable of totally internally reflecting light that enters said detecting surface at an angle greater than a $\theta_{min}$, (c) a plurality of annular apertures corresponding to the plurality of optical elements such that light entering the detecting surface at an angle less than $\theta_{min}$ impinges on the aperture, and (d) a detector. In useful embodiments, the excitation light source is a laser diode. In other embodiments, the chip comprises a polymer having a refractive index of about 1.45-1.65 and the $\theta_{min}$ is about 62°. Particularly useful chips are made from ZEONEX. Useful detectors include CMOS detectors and CCD cameras. In useful embodiments, the luminescent sensor configuration comprises an excitation light source that directs an excitation beam through the chip onto the detection moiety, thus, illuminating the detection moiety from "below". Desirably, the excitation beam is aligned with the optical axis of the optical elements and is done so by being reflected from a mirror (e.g., the dichroic mirror) onto the detection moiety.

By "optically coupled," when referring to the relationship between a moiety and an optical element, includes but is not limited to luminescent molecules directly bound to or adsorbed onto the optical element; luminescent molecules indirectly attached to the optical element through one or more linker molecules; luminescent molecules entrapped within a film (e.g., a polymer or sol-gel matrix) that is coated onto the optical element; a non-luminescent molecule that is capable of binding to a luminescent molecule of interest.

By "$\theta_{min}$" is meant the minimum angle that light incident to the surface of the optical element is capable of entering the optical element and being substantially totally internally reflected such that the incident light is substantially collimated and directed toward the detector.

BRIEF DESCRIPTION OF THE DRAWINGS

The foregoing and other features and advantages of the present disclosure will be more fully understood from the following detailed description of the exemplary embodiments, taken in conjunction with the accompanying drawings in which.

DETAILED DESCRIPTION OF THE EXEMPLARY EMBODIMENTS

The present invention is a polymeric optical chip for the parallel and highly efficient detection of surface-generated fluorescence. The chip takes advantage of the large angle optics of solid parabolic optical elements and may be used for biodiagnostics including, for example, "lab-on-a-chip" applications. As described in more detail below, the optical chip is designed for the parallel real-time readout of surface-bound fluorescence obtained from biochemical reactions. Fluorescence is obtained from an array of optical elements, each having a receptive molecule optically coupled to its surface. The receptive molecule is capable of detecting the analyte of interest, wherein detection results in luminescence radiated into the optical element. Each optical element in the array may be coated with the same or different detection moiety and is varied by the user based on the analyte of interest. For convenience, the combination of the analyte of interest and the receptive molecule will be referred to as merely as the analyte unless specifically noted.

The array enhances the fluorescence collection to a higher efficiency than is obtained using an N.A. 1.3 microscope objective. The array elements accomplish optics with very high surface angles and thus allow for supercritical angle fluorescence (SAF) collection and total internal reflection fluorescence (TIRF) excitation. In particularly useful embodiments, the array is made by polymer injection molding, allowing for inexpensive mass production of these optical chips. The optical chip of this invention is based on an understanding of the anisotropic emission properties of electric dipoles (fluorophores) close to a dielectric interface. The optical elements of the chip have a simple but highly efficient optical geometry to collect surface-bound fluorescence.

Figure 1:
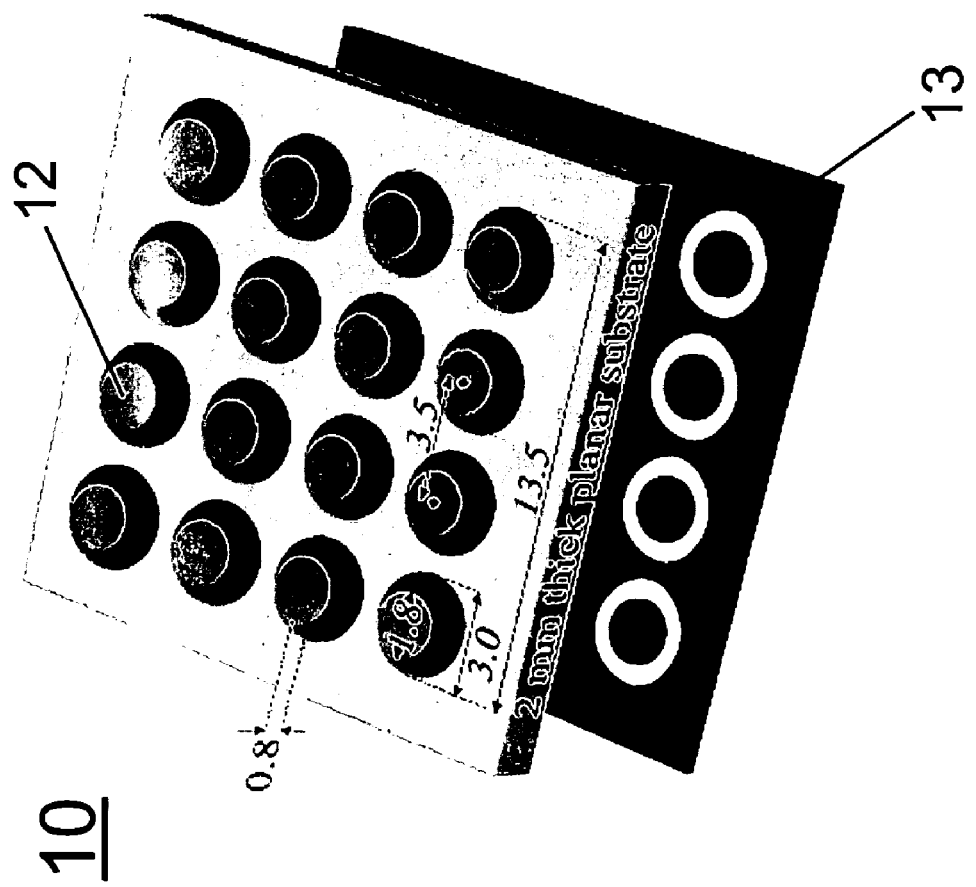
FIG. 1 is a perspective view of an optical chip constructed in accordance with the principles of the present disclosure, wherein the optical chip contains a 4×4 array of optical elements.

Turning now to the figures, wherein like components are designated by like reference numerals throughout the several views. FIG. 1 illustrates the basic design of the optical chip 10 of the present invention. The optical elements 12 are typically arranged in an array. FIG. 1 illustrates the optical elements 12 arranged in a symmetrical 4×4 array; however, an array of any convenient dimension for number of optical elements 12 may be created depending upon the specific application. Further, the individual optical elements 12 of FIG. 1 are shown as being of identical dimension. This need not always be the case. Optical elements 12 of various sizes and shapes may be used in accordance with the principles of this invention and will depend upon the specific applications for which the optical chip 10 is designed.

Figure 2:
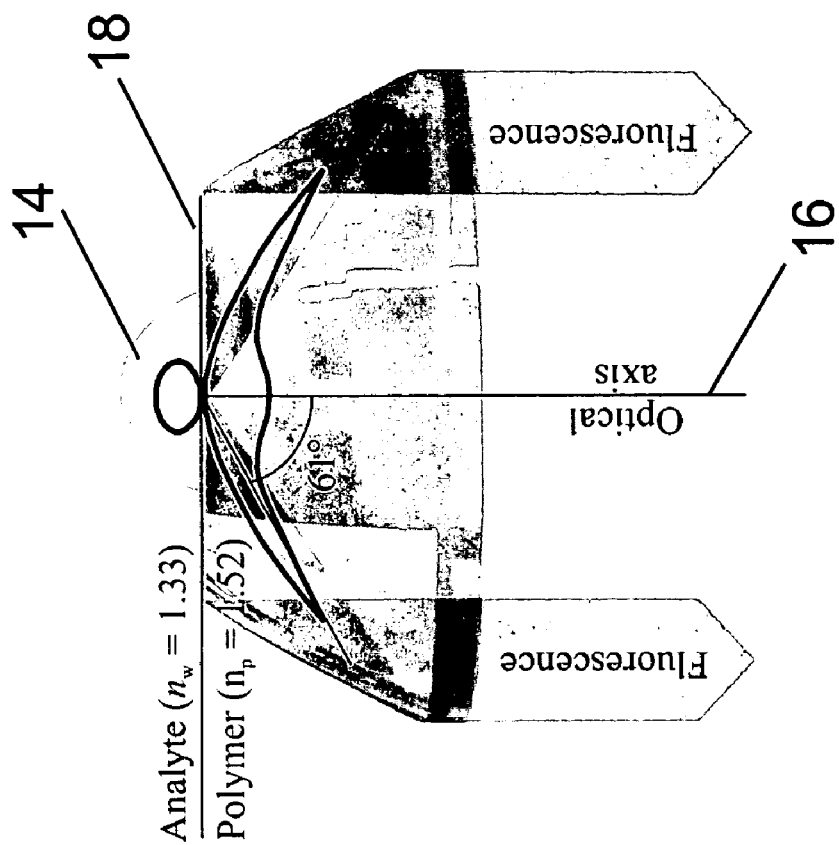
FIG. 2 is a schematic cross-section of an optical element according to the principles of the present disclosure.

FIG. 2 illustrates a single optical element 12. Optical elements 12 are solid and parabolic, and operate by total internal reflection in order to convert the strong intensity maximum emitted by the analyte 14 from large surface angles into collimated and conveniently detectable rays along the optical axis 16. The polymer interface 18 is the detection surface of the optical element 12 that is exposed to the analyte-containing solution.

In order to achieve the desired properties, the polymeric optical elements (and optical chip) must have a sufficiently high refractive index relative to the analyte-containing solution (usually aqueous). Desirably, the refractive index of the polymer ($n_p$) is about 1.45-1.65. Because the optical chip and detection system of this disclosure is highly sensitive, it is assumed that the analyte-containing solution will be dilute and have a refractive index close to that of water ($n_w$=1.33). However, the chip may be used with concentrated solutions of analyte and complex biological fluids such as blood, urine, saliva, and the like. Additionally, the chip may be used with non-aqueous solution of analyte. Of course, the polymer selection is primarily based on its refractive index and can be varied for analyte solutions having different refractive indices in accordance with the principles of this disclosure.

One approach to detect very low analyte concentrations are affinity-based assays using surface-bound receptive molecules. For the readout of such assays, a strict confinement of the detection volume to the surface is important because the signal from unbound ligands in bulk solution above the detection surface 18 adds to the background of the measurement. In this context, it is advantageous that the parabolic optical element 12 is designed for large angle optics exceeding the critical angle of the water/polymer interface (i.e., 61° in FIG. 2). Only luminescent molecules located directly in front of the polymer interface 18 of optical element 12 are capable of emitting fluorescence above the critical angle into the optical element 12. Consequently, exclusive collection of supercritical angle fluorescence (SAF) strictly confines the detection volume to the surface allowing for real-time measurements of surface assays (e.g., in a flow cell).

The fluorescent light that enters the optical element 12 at an angle between $\theta_{min}$ and $\theta_{max}$ is retained, collimated, and directed toward the detector as a result of total internal reflection. The range of entry angles that fall between $\theta_{min}$ and $\theta_{max}$ that are subsequently detected is set by the presence of an annular aperture 13 located below the optical element 12. Usually the annular apertures 13 are present as an array below the optical chip 10, matching the array of optical elements 12. The light propagating inside the optical element 12 that impinge on the liquid-polymer interface at angles greater than $\theta_{min}$ is totally reflected within the optical chip 10. The parabolic shape ensures that the internally reflected light is substantially collimated and directed along the optical axis perpendicular to the detection interface. The opaque center of the annular aperture 13 prevents fluorescent light or other background radiation that enters the optical element at an angle less than $\theta_{min}$ from reaching the detector. This effectively filters out light that originates anywhere other than the detection surface 18, including light originating in the bulk solution above the optical element 12. Other principles of internal reflection, high angle optics, and fluorescent detector design are discussed in WO 02/059583, WO 03/023377, and U.S. Pat. No. 6,714,297, each of which is hereby incorporated by reference.

The optical chip 10 of this invention may also be used in conjunction with total internal reflection fluorescence (TIRF). At TIRF, the excitation light needs to be incident above the critical angle, using the thin evanescent field at the surface to selectively excite surface-bound fluorescence. The optical element 14 may be used to excite the fluorescence above the critical angle and accomplish objective-type TIRF. Such applications typically require the use of microscope objectives with high numerical apertures (e.g., N.A.≧1.45).

Although the optical chip 10 of FIG. 1 is shown with particular dimensions, it may be scaled to any useful size depending upon the requirements of the final application. Usefully, the optical chip 10 is scaled to millimeter dimensions and integrated into small polymer sensor chips allowing for parallel detection of a large number of analytes. One or more optical chips 10 may be integrated into a sensor chip.

The optical elements 12 are capable of focusing a parallel beam of fluorescent light down to a small surface spot of sub micrometer dimensions. This however should be avoided in the design and dimensions of the optical elements 12 in order to prevent photobleaching of the detector and to average out surface inhomogeneities. Desirably, the optical elements 12 focus onto larger surface areas.

EXAMPLE 1

Disposable Biochip

Figure 3:
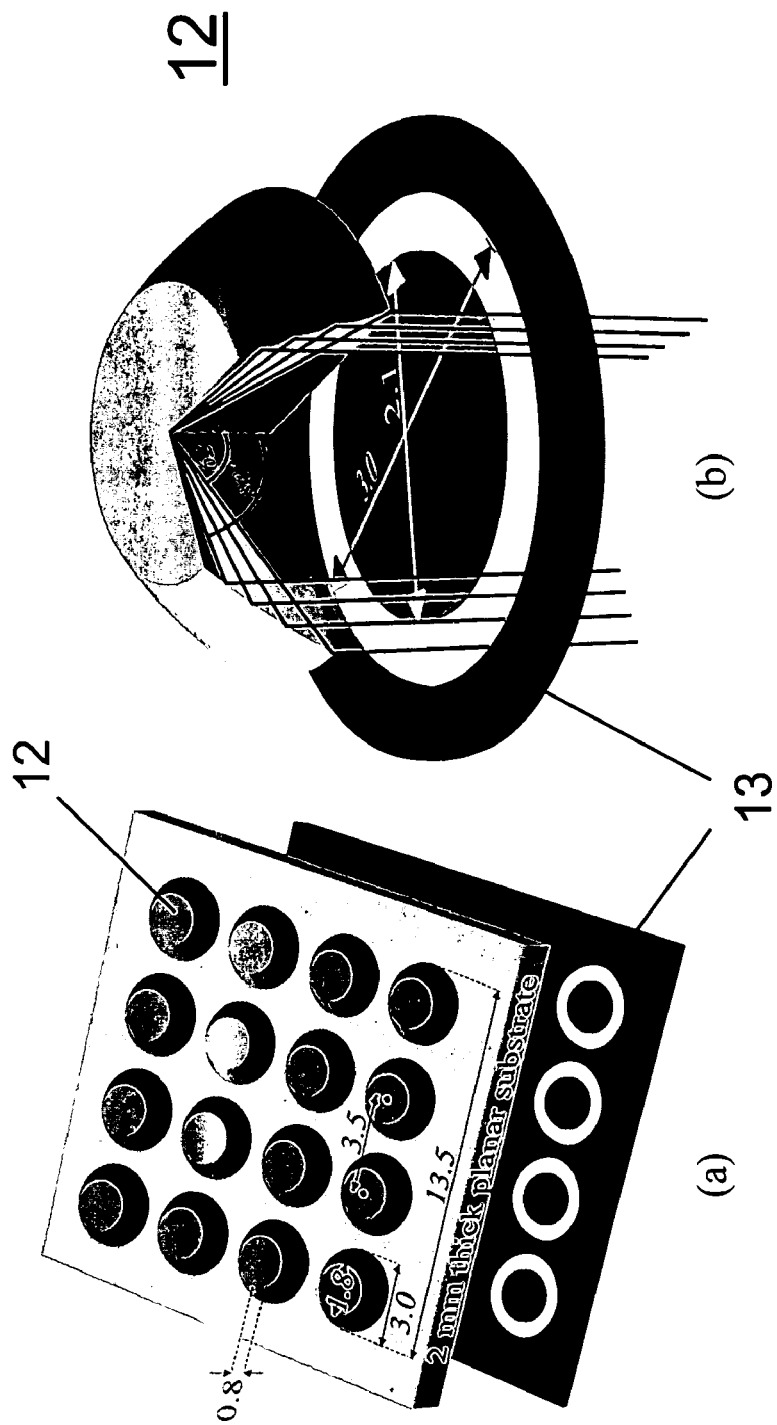
FIG. 3A is a perspective view of an optical chip constructed in accordance with the principles of the present disclosure, including the annular apertures below the chip.
FIG. 3B is a cut-away perspective view of an optical element from the optical chip shown in FIG. 3A, including an annular aperture.

FIG. 3A illustrates one exemplary configuration of the optical chip 10 of this invention. The optical chip 10 is formed by injection molding as a single element. It has a 2 mm thick planar base and a 4×4 array of optical elements 12. Each optical element 12 is has a paraboloid shape with a lower diameter of 3.0 mm, an upper diameter of 1.81 mm, and a height of 0.8 mm. The optical elements 12 are spaced 3.5 mm center-to-center. With a focal length of $f_p$=0.45 mm, the geometrical focus of each optical element 12 lies exactly at its upper surface. An annular aperture 13 below each optical element 12 sets the range of accessible surface angles from $\theta_{min}$=62° to $\theta_{max}$=80°. The low angle limit is chose to obtain purely supercritical angles and the large angle limit is chosen because the fluorescence emission approaches zero for the surface angle approaching 90° (see FIG. 3B). This range of angles is used for both fluorescence excitation and fluorescence collection. The material of the chip is ZEONEX (Zeon Corp., Japan) and is characterized as having very low auto fluorescence and is suitable for injection molding. ZEONEX has a refractive index of $n_d$=1.52. The fluorescence collection efficiency of the optical element 12 was calculated according to the method of Enderlein et al. (*Appl. Opt.* 38: 724-732, 1999) to be 32% (i.e., nearly one third of the overall fluorescence emission is captured). For comparison, an N.A. 1.3 microscope objective collects the light within a cone of up to 59°. The portion of the surface-generated fluorescence emitted into this cone is also 32%. However, when the optical losses that occur in such high N.A. objectives are taken into account, each parabolic element exhibits a superior collection efficiency.

Figure 4:
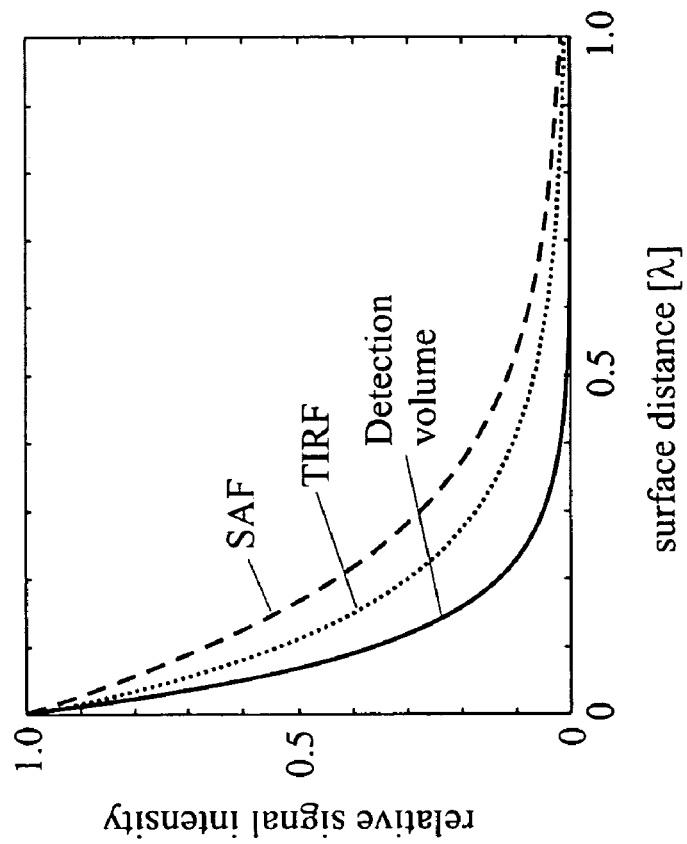
FIG. 4 is a graph showing the normalized decay of the fluorescence detection efficiency.

The configuration shown in FIG. 3A illuminates the analyte from below with the excitation light. The $\theta_{min}$ of the interface between the polymer of the optical element 12 and the aqueous analyte is 61°. In this geometry, fluorescence excitation and fluorescence collection is performed above the critical angle. FIG. 4 shows that the combination of SAF collection and TIRF excitation causes the detection volume to decay steeper into the aqueous analyte than by either technique alone because the distance dependent decay of the detection volume is the product of both decays (the SAF decay and the TIRF decay). At a surface distance of 0.1 wavelengths (λ), the detection efficiency is reduced to about 1/e of the surface value.

Figure 5:
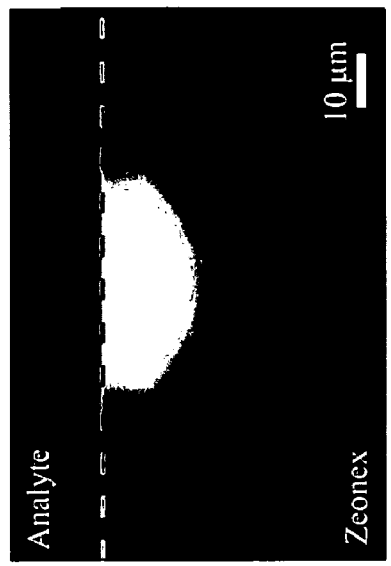
FIG. 5 is a contour plot of the detection volume of an optical element.

The detection volume obtained for a 2.0 mm excitation aperture 54 (see FIG. 6 and Example 2) is shown in FIG. 5. The penetration depth of the detection volume into the solution of ~60 nm (distance where intensity decayed to 1/e) is too short to become visible in the chosen length scale. On the side of the polymer, the detection volume only expands about 10 μm. For highly sensitive fluorescence detection, such a small overall detection volume is important because it reduces or eliminates background from scattered light.

EXAMPLE 2

Biochip Reader

Figure 6:
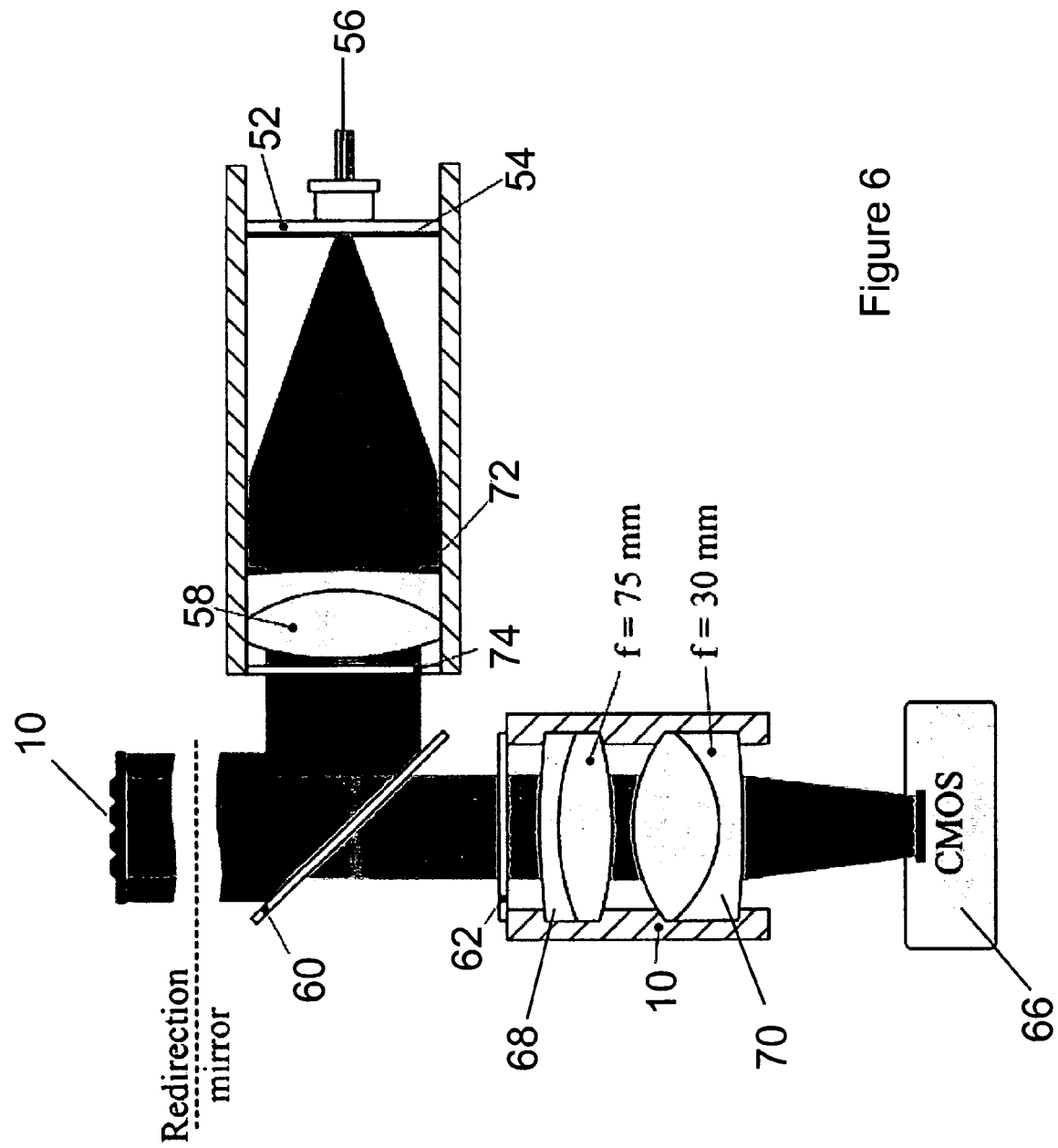
FIG. 6 is a schematic diagram of a fluorescence detector that incorporates an optical chip constructed in accordance with the principles of the present disclosure.

As described above, the core of the optical chip 10 is the array of optical elements 12. The array delivers a nearly collimated fluorescence signal when illuminated with (nearly) collimated laser light. FIG. 6 is a schematic diagram of one possible arrangement of elements using the optical chip 10 to detect and measure fluorescence. Of course, other arrangements of the same or different elements are possible within the principles of this invention. FIG. 6 illustrates that a diffusing plate 52, an excitation aperture 54 in front of a laser diode 56 (e.g., 635 nm, HL6319G, Hitatchi) of circular emission profile introduces a desired beam divergence and generates a nearly homogenous emission into the angles ±10° with respect to the optical axis. An achromatic lens doublet 58 (f=50 mm) with a 20 mm aperture 72 and optional excitation filter 74, produces a nearly collimated beam, which is redirected by a dichroic mirror 60, that illuminates the optical chip 10 from below. Each optical element 12 focuses the beam on the surface and converts surface-generated fluorescence into nearly parallel rays. The fluorescence emitted into the surface angles 62°-80° exits the optical chip 10 downward. Optionally, an annular aperture may be used as described above. Desirably, the annular aperture is place between the dichroic mirror 60 and the CMOS detector 66, but may also be placed between the dichroic mirror 60 and the chip 10. An achromatic lens doublet 64 (with optional emission filter 62) images the fluorescence signal from the optical chip 10 onto a CMOS detector 66 with a demagnification ratio of 2.5. The distance between the optical array 10 and the front side lens 68 (f=75 mm) of the lens doublet 64 is 70.4 mm and the distance between the back side lens 70 (f=30 mm) of the lens doublet 64 and the CMOS detector 66 is 22.2 mm. The dimensions of the sensitive area of the CMOS detector 66 are 8.6×6.9 mm. The optical chip 10 is designed to fit into a housing of 15×15×5 cm.

Proper alignment and configuration of the excitation optics is critical to maximize fluorescence detection. For optimum performance, the optical elements 12 should be illuminated with excitation light aligned to their optical axis. Desirably, this is performed using an adjustable mirror below the optical chip 10.

The optical elements 12 are capable of focusing a parallel beam of fluorescent light down to a small surface spot of sub micrometer dimensions. This however should be avoided in the design and dimensions of the optical elements 12 in order to prevent photobleaching of the detector and to average out surface inhomogeneities. Desirably, the optical elements 12 focus onto larger surface areas. Likewise, the size of the foci generated on the top of the parabolic elements can be increased by decreasing the collimation of the excitation beam. Such angular deviations can be introduced in a defined manner by using a diffusing plate 52 (±10° diffusing angle) and an excitation aperture 54. The excitation aperture 54 generates a bright light disc whose diameter determines the size of the focus generated by the optical elements 12. The focus size increases with increased disc diameter. The dimensions of the focus should not be arbitrarily enlarged because, as fluorescence emitted to far away from the geometrical foal point of the optical element 14 cannot be fully captured.

Off-axis fluorescence emission is not perfectly collimated which leads to a fractional loss at the aperture limit of the achromatic doublet 64. The degree of leakage is not identical for all parabolas (optical elements 12) but depends on their position in the array and is highest for the outer elements. Consequently, too large an excitation aperture 54 leads to inhomogeneous collection efficiencies across the array and should be avoided.

Figure 7:
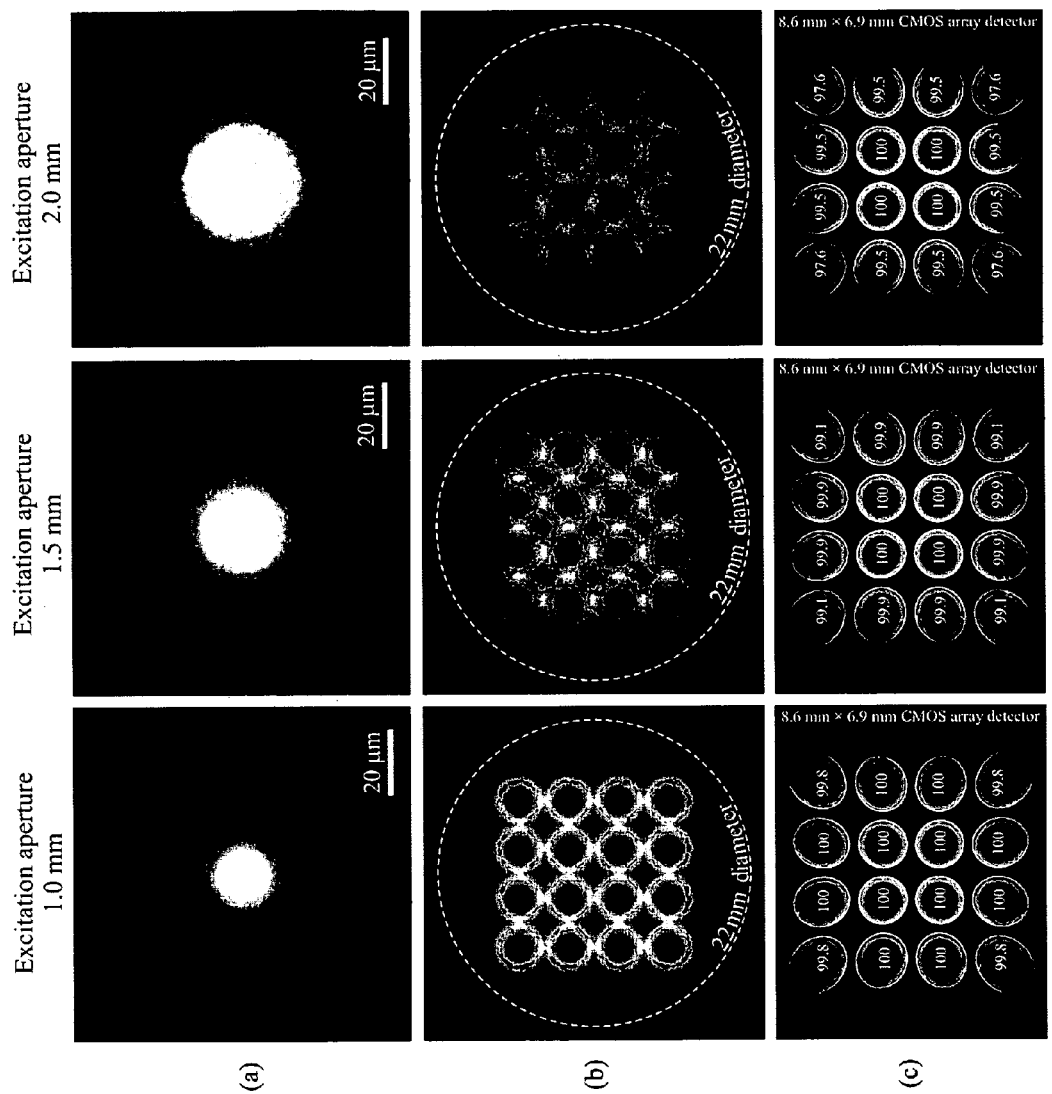
FIG. 7A is a raytracing simulation of the focal point of an optical element for varying excitation aperture diameters.
FIG. 7B is a raytracing simulation of the fluorescence intensity observed at the entrance of the achromatic double shown in FIG. 6 for varying excitation aperture diameters.
FIG. 7C is a raytracing simulation of the fluorescence images on the CMOS detector shown in FIG. 6 for varying excitation aperture diameters.

In order to determine a suitable excitation aperture 54 diameter, the optical chip 10 was simulated using a raytracing procedure. FIG. 7A shows the dimensions of the illuminated areas at the geometrical focal points of the parabolic optical elements 12 for three different diameters of excitation apertures 54. It was assumed that the laser beam illuminates the excitation aperture 54 homogeneously. The illustrated distribution for each aperture diameter is representative for all 16 foci produced from the 4×4 array described above. The illuminated surface areas are 23 μm, 35 μm, and 49 μm (FWHM) for apertures of (1.0 mm, 1.5 mm, and 2.0 mm), respectively.

FIG. 7B shows the simulated fluorescence intensity at the entrance of the achromatic doublet 64. A homogeneous distribution of surface-bound fluorescence analyte was assumed. The images were obtained by raytracing, taking the anisotropic emission of surface-generated fluorescence into account by weighting the fluorescence rays according to the angular distribution of emission shown in FIG. 2. The increase of illuminated surface area leads to less collimated fluorescence rays and to an increasingly diffuse fluorescence distribution at the entrance of the achromatic doublet 64. All fluorescence rays that impinge outside the clear aperture of 22 mm diameter are lost. Such loss occurs in particular at the outer optical elements 12 with a 2 mm excitation aperture.

FIG. 7C shows the fluorescence intensity distribution on the CMOS array 66. The numbers give the percentage of fluorescence intensity on the camera to the fluorescence collimated by the optical elements 12. For the studied excitation aperture 54 sizes, 100% of the fluorescence rays from the inner four optical elements 12 are transmitted through the optics, whereas a certain loss occurs for the outer optical elements 12. Optical losses due to reflections at surfaces and filters were neglected. In case of an aberration-free optics the rings would be of circular shape. The image distortion is a result of the fairly high f-number (3.08) of the achromatic doublet 64. Because of the non-circular intensity distribution of the outer optical elements 12, it is necessary to integrated the fluorescence intensity to determine the analyte concentrations. Together, these results demonstrate that excitation apertures 54 up to 2 mm introduce a signal deviation of <2.5% throughout the 4×4 array.

All publications mentioned in this specification are herein incorporated by reference to the same extent as if each independent publication was specifically and individually indicated to be incorporated by reference.

Although the foregoing present disclosure has been described in some detail by way of illustration and example for purposes of clarity of understanding, it will be readily apparent to those of ordinary skill in the art in light of the teachings of this present disclosure that certain changes and modifications may be made thereto without departing from the spirit or scope of the appended claims.

What is claimed is:

1. An optical chip comprising a plurality of optical elements, wherein said optical elements, comprising:
  a solid parabolic shape such that light entering said optical element at a detection surface at an angle greater than a $\theta_{min}$ is totally internally reflected and substantially collimated along the axis perpendicular to said detection surface;
  a detection moiety optically linked to said detection surface;
  a corresponding annular aperture axially aligned with said optical elements, and wherein said optical chip comprises a polymer having a refractive index greater than the refractive index of water.

2. The optical chip of claim 1, wherein said annular aperture is configured such that light entering said optical element at an angle less than said $\theta_{min}$ impinges on an opaque element of said aperture.

3. The optical chip of claim 1, wherein said $\theta_{min}$ is about 62°.

4. The optical chip of claim 1, wherein said refractive index is about 1.45-1.65.

5. The optical chip of claim 1, wherein said polymer is a cyclic polyolefin.

6. The optical chip of claim 1, wherein said detection moiety is an antibody, an antibody fragment or an oligonucleotide.

7. A luminescent sensor configuration comprising:
  an excitation light source;
  a chip comprising a plurality of solid parabolic optical elements, wherein each optical element includes a detection moiety optically linked to a detecting surface, and is capable of totally internally reflecting light that enters said detecting surface at an angle greater than a $\theta_{min}$;
  a plurality of annular apertures corresponding to said plurality of optical elements and axially aligned with said optical elements such that light entering said detecting surface at an angle less than $\theta_{min}$ impinges on an opaque element of said aperture; and a detector.

8. The luminescent sensor configuration of claim 7, wherein said excitation light source is a laser diode.

9. The luminescent sensor configuration of claim 7, wherein said chip comprises a polymer having a refractive index is about 1.45-1.65.

10. The luminescent sensor configuration of claim 7, wherein said chip comprises a cyclic polyolefin.

11. The luminescent sensor configuration of claim 7, wherein said $\theta_{min}$ is about 62°.

12. The luminescent sensor configuration of claim 7, wherein said detector is a CMOS detector or a CCD camera.

13. The luminescent sensor configuration of claim 7, wherein said detection moiety is an antibody, antibody fragment, or an oligonucleotide.

14. The luminescent sensor configuration of claim 7, wherein said excitation light source directs an excitation beam through said chip onto said detection moiety.

15. The luminescent sensor configuration of claim 14, wherein said excitation beam is aligned with the optical axis of said optical elements.

16. The luminescent sensor configuration of claim 14, wherein said excitation beam is reflected from a mirror onto said detection moiety.

* * * * *